US008757496B2

(12) United States Patent
Watanabe

(10) Patent No.: US 8,757,496 B2
(45) Date of Patent: Jun. 24, 2014

(54) BIOLOGICAL SAMPLE MEASURING DEVICE AND BIOLOGICAL SAMPLE MEASURING SENSOR USED IN SAME

(75) Inventor: Atsushi Watanabe, Ehime (JP)

(73) Assignee: Panasonic Healthcare Co., Ltd., Ehime (JP)

( * ) Notice: Subject to any disclaimer, the term of this patent is extended or adjusted under 35 U.S.C. 154(b) by 0 days.

(21) Appl. No.: 13/824,769

(22) PCT Filed: Oct. 19, 2011

(86) PCT No.: PCT/JP2011/005842
§ 371 (c)(1),
(2), (4) Date: Mar. 18, 2013

(87) PCT Pub. No.: WO2012/053199
PCT Pub. Date: Apr. 26, 2012

(65) Prior Publication Data
US 2013/0175344 A1 Jul. 11, 2013

(30) Foreign Application Priority Data
Oct. 19, 2010 (JP) .................................. 2010-234307

(51) Int. Cl.
*G06K 7/12* (2006.01)
(52) U.S. Cl.
USPC .......................................... 235/469; 235/375
(58) Field of Classification Search
USPC .......................... 235/469, 375, 435, 438, 446
See application file for complete search history.

(56) References Cited

U.S. PATENT DOCUMENTS

| 7,695,608 | B2 | 4/2010 | Kim et al. | |
| 8,277,635 | B2 | 10/2012 | Kim et al. | |
| 2002/0060247 | A1 | 5/2002 | Krishnaswamy et al. | |
| 2005/0178663 | A1 | 8/2005 | Kobayashi | |
| 2006/0292039 | A1* | 12/2006 | Iida | 422/82.05 |
| 2007/0081920 | A1 | 4/2007 | Murphy et al. | |
| 2010/0032321 | A1 | 2/2010 | Kim et al. | |
| 2011/0124116 | A1* | 5/2011 | Wohlstadter et al. | 436/172 |
| 2012/0029326 | A1* | 2/2012 | Kawamura et al. | 600/310 |

FOREIGN PATENT DOCUMENTS

| CN | 1948952 A | 4/2007 |
| CN | 101275925 A | 10/2008 |
| CN | 101627304 A | 1/2010 |
| JP | 2001-351139 A | 12/2001 |

(Continued)

OTHER PUBLICATIONS

International Search Report for PCT/JP2011/005842 dated Jan. 10, 2012.

(Continued)

*Primary Examiner* — Edwyn Labaze
(74) *Attorney, Agent, or Firm* — Pearne & Gordon LLP

(57) ABSTRACT

The purpose of the present invention is to reduce costs for biological sample measurement devices by means of providing a novel method for easily and reliably identifying types of biological sample measurement sensors. Specifically, the present invention provides a biological sample measurement device provided with a main body case, a sensor insertion port, a connector, a light-emitting element and a light-receiving element disposed inside of the main body case in the vicinity of the connector, and a connector terminal. The light-emitting element can irradiate light onto a biological sample measurement sensor attached to the connector. The light-receiving element can receive reflected light or transmitted light from the biological sample measurement sensor attached to the connector. The type of the biological sample measurement sensor is identified on the basis of the light received and recognized by the light-receiving element.

11 Claims, 15 Drawing Sheets

(56) References Cited

FOREIGN PATENT DOCUMENTS

| | | |
|---|---|---|
| JP | 2002-521692 A | 7/2002 |
| JP | 2006-285659 A | 10/2006 |
| JP | 2010-520463 A | 6/2010 |
| WO | 03/076918 A1 | 9/2003 |

OTHER PUBLICATIONS

Chinese Office Action for Application No. 201180050361.1 dated Mar. 21, 2014.

* cited by examiner

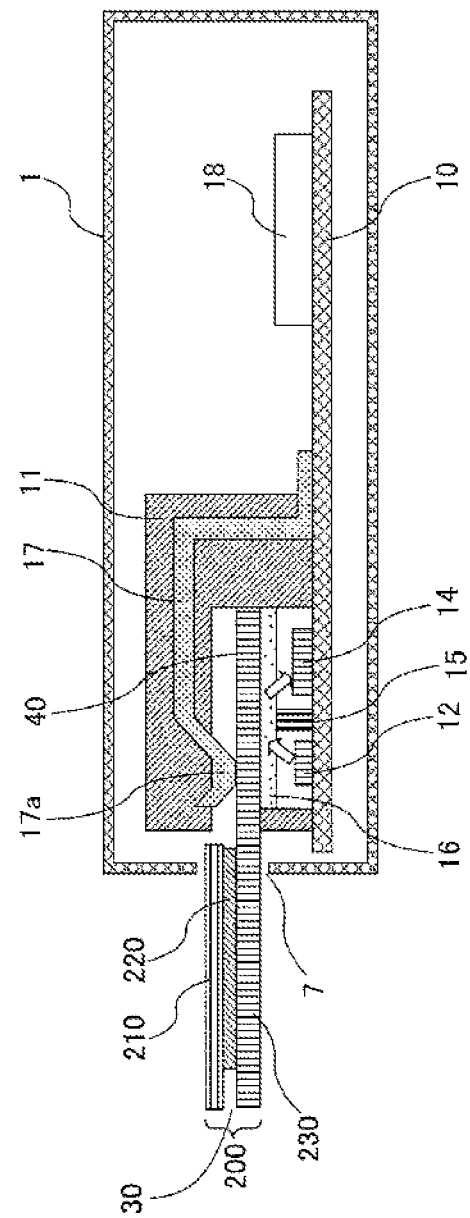

BIOLOGICAL SAMPLE MEASURING DEVICE AND BIOLOGICAL SAMPLE MEASURING SENSOR USED IN SAME

TECHNICAL FIELD

The present invention relates to a biological sample measurement device for measuring biological samples for blood glucose levels, lactic acid levels and/or the like, and a biological sample measurement sensor to be used in the measurement device.

BACKGROUND ART

Conventional biological sample measurement devices are composed of, for example, a main body case, a connector which is disposed in the main body case for attachment of a biological sample measurement sensor, and a barcode reader (see PTL 1). The conventional biological sample measurement device is configured to read a barcode displayed on a biological sample measurement sensor connected to the connector by means of a barcode reader for the determination of the type of the biological sample measurement sensor, and conduct biological sample measurement that is unique to the biological sample measurement sensor.

CITATION LIST

Patent Literature

PTL 1
Japanese Unexamined Patent Application Publication (Translation of PCT Application) No. 2002-521692

SUMMARY OF INVENTION

Technical Problem

The barcode reader that reads the type of a biological sample measurement sensor requires a mechanism that scans light and a mechanism that reads information of the scanned light. Accordingly, the cost of a biological sample measurement device including a barcode reader tends to be high. In this respect, the present invention aims to reduce the cost of biological sample measurement devices by providing a novel technique for easily and accurately determining the types of biological sample measurement sensors.

Solution to Problem

In order to achieve the foregoing object, the present invention provides a biological sample measurement device including: a main body case; a sensor insertion port that is disposed in the main body case and used for inserting a biological sample measurement sensor; a connector that is disposed in the main body case and to which the biological sample measurement sensor is to be attached; a light-emitting element and a light-receiving element that are disposed in the vicinity of the connector in the main body case; and a connector terminal that is disposed in the main body case and can be connected to a connection terminal section of the biological sample measurement sensor attached to the connector. The light-emitting element can emit light to the biological sample measurement sensor to be attached to the connector, and the light-receiving element can receive light reflected from or transmitted through the biological sample measurement sensor to be attached to the connector. Based on the light received and recognized by the light-receiving element, the type of the biological sample measurement sensor is determined. With this configuration, the intended purpose is accomplished.

Advantageous Effects of Invention

As described above, in the biological sample measurement device of the present invention, the light-receiving element receives light reflected from or transmitted through the biological sample measurement sensor attached to the connector, whereby the type of the biological sample measurement sensor can be determined. This eliminates the need to provide means for scanning light and/or means for reading the scanned light, which have been employed in the art. Consequently, it is possible to reduce the cost of the biological sample measurement device.

BRIEF DESCRIPTION OF DRAWINGS

FIG. 7 is a main part cross-sectional view of the vicinity of a connector of a biological sample measurement device of Embodiment 1;

DESCRIPTION OF EMBODIMENTS

Biological Sample Measurement Device

A biological sample measurement device of the present invention includes a main body case, a sensor insertion port, a connector, a light-emitting element, a light-receiving element, and a connector terminal.

Figure 1:
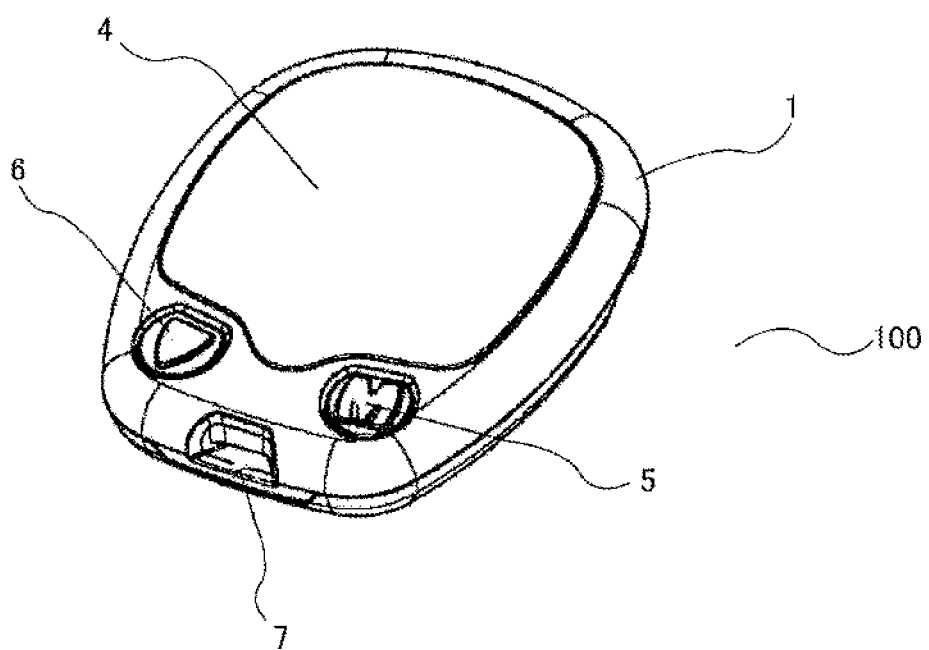
FIG. 1 is a perspective view showing the exterior of a biological sample measurement device.

FIG. 1 is a top perspective view showing the exterior of an example of the biological sample measurement device. As shown in FIG. 1, biological sample measurement device 100 includes main body case 1, display section 4, power switch 5, scroll switch 6 for scrolling the contents to be displayed on display section 4, and sensor insertion port 7. Display section 4 displays a measurement result and/or the like. Power switch 5 is a switch for turning on or off the power of the measurement device. Through sensor insertion port 7, a biological sample measurement sensor can be inserted into main body case 1.

Figure 2:
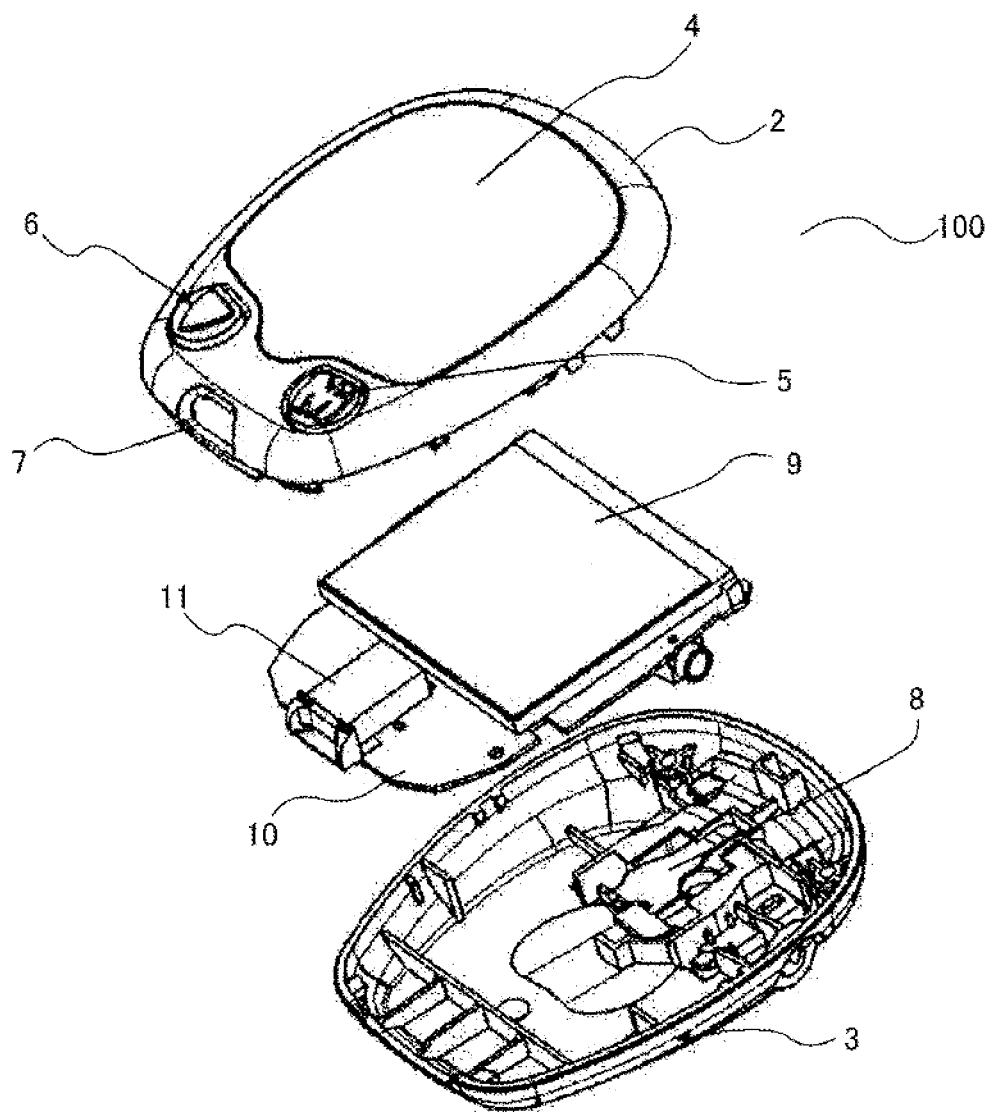
FIG. 2 is an exploded perspective view of the biological sample measurement device.

FIG. 2 is an exploded perspective view of biological sample measurement device 100. Main body case 1 is composed of top cover 2 and bottom cover 3. Display section 4 is disposed on the top surface of top cover 2, and power switch 5 and scroll switch 6 for scrolling the contents to be displayed on display section 4 are disposed in front of display section 4. In addition, sensor insertion port 7 is disposed in front of scroll switch 6. Battery 8 as a power source is stored in bottom cover 3.

Liquid crystal display element 9 is disposed between top cover 2 and bottom cover 3 and displays information on display section 4. Moreover, control board 10 is disposed in front of liquid crystal display element 9. Connector 11 is disposed on control board 10, and a biological sample measurement sensor inserted through sensor insertion port 7 is attached to connector 11.

Connector 11 disposed in the main body case is an attachment section for attaching a biological sample measurement sensor to biological sample measurement device 100. When a biological sample measurement sensor is attached to connector 11, a connector terminal of connector 11 is electrically connected to a connection terminal section of the biological sample measurement sensor (see FIGS. 7 and 12).

A light-emitting element and a light-receiving element are disposed in the vicinity of connector 11. The light-emitting element is not particularly limited, and it is, for example, an LED light-emitting element. The biological sample measurement sensor attached to connector 11 is irradiated with light emitted from the light-emitting element.

Figure 12:
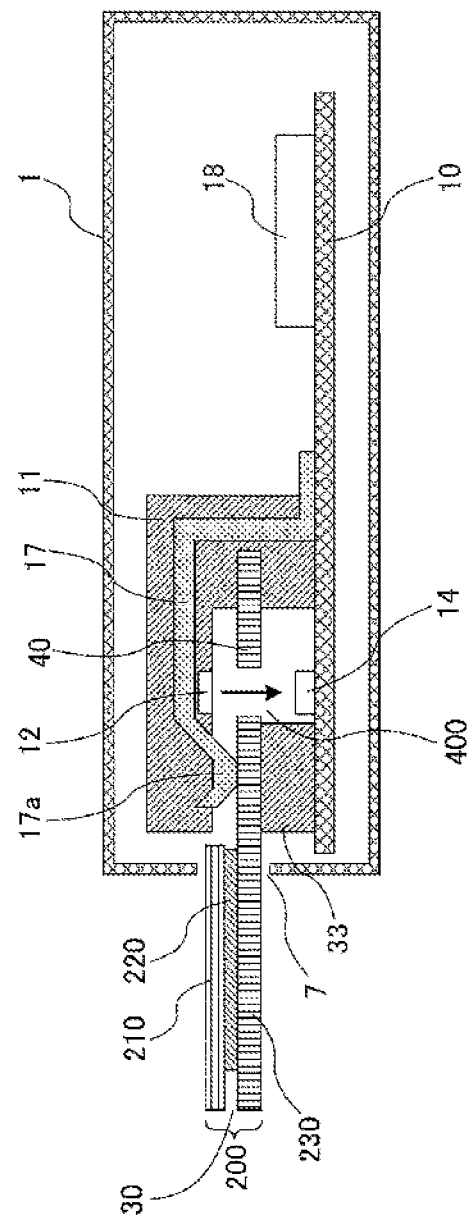
FIG. 12 is a main part cross-sectional view of the vicinity of a connector of a biological sample measurement device of Embodiment 2.

The light-receiving element receives 1) light which is emitted from the light-emitting element and then reflected from the biological sample measurement sensor (see FIG. 7), or 2) light which is emitted from the light-emitting element and then passes through the biological sample measurement sensor (see FIG. 12). The biological sample measurement device of the present invention is characterized by determining the type of a biological sample measurement sensor based on the light received by the light-receiving element.

In a first specific embodiment (see Embodiment 1), at least a portion of the biological sample measurement sensor is formed in advance to have a colored section (see FIG. 10), so that the light emitted from the light-emitting element is applied to the colored section and the light reflected from the colored section is received by a color sensor (FIG. 7). In a second specific embodiment (see Embodiment 2), a light-transmissive section is disposed in advance in the biological sample measurement sensor (see FIG. 15), so that light from the light-emitting element passes through the light-transmissive section and the light passed through the light-transmissive section is received by a photodiode (see FIG. 12).

[Biological Sample Measurement Sensor]

The biological, sample measurement sensor of the present invention electrochemically measures, for example, a substrate in a biological sample. For example, the biological sample measurement sensor measures blood glucose level or lactic acid level.

Figure 3:
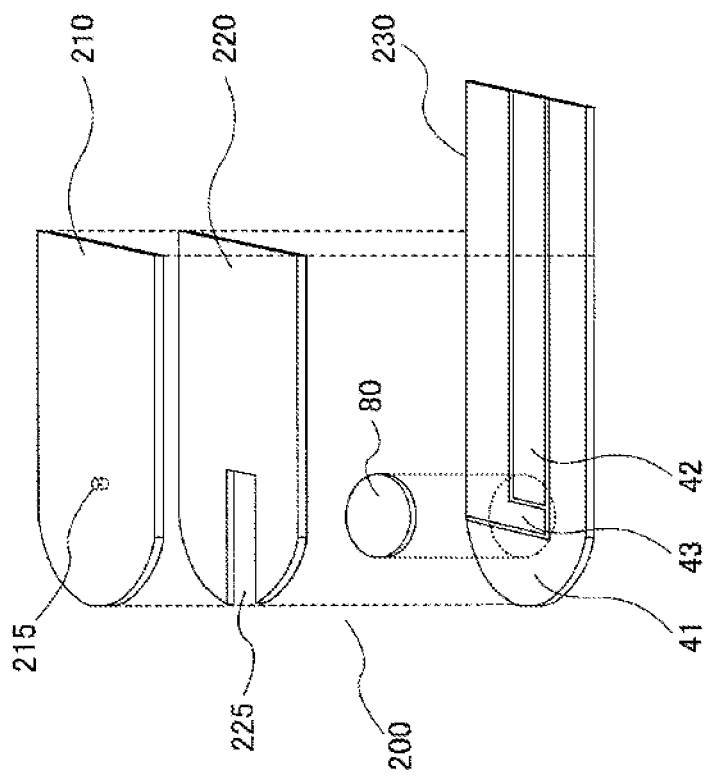
FIG. 3 is an exploded perspective view of a biological sample measurement sensor to be attached to the biological sample measurement device.
Figure 4:
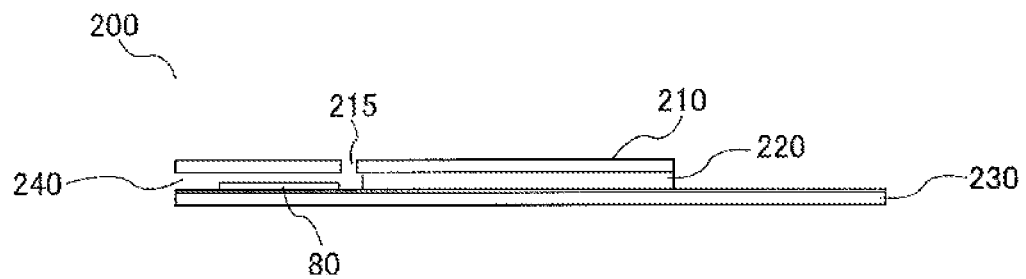
FIG. 4 is a cross-sectional view of the biological sample measurement sensor to be attached to the biological sample measurement device.
Figure 5:
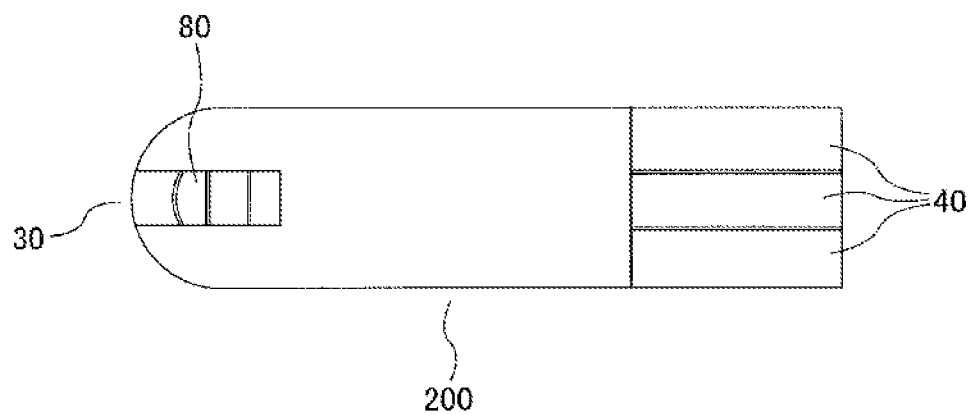
FIG. 5 is a plan view of the biological sample measurement sensor to be attached to the biological sample measurement device, the biological sample sensor having no cover provided thereon.

FIGS. 3 to 5 show an example of biological sample measurement sensor 200. FIG. 3 is an exploded perspective view of biological sample measurement sensor 200; FIG. 4 is a cross-sectional view of biological sample measurement sensor 200; and FIG. 5 is a plan view showing biological sample measurement sensor 200 without cover 210. As shown in FIGS. 3 to 5, biological sample measurement sensor 200 is a plate-like member.

As shown in FIG. 5, biological sample measurement sensor 200 includes biological sample inlet 30 disposed at one end of the sensor for injection of a biological sample by landing a droplet of the sample on the inlet, and connection terminal section 40 (where an electrode terminal is disposed) disposed at the other end of the sensor. As shown in FIG. 3, biological sample measurement sensor 200 includes cover 210, spacer 220, and sensor base 230.

Sensor base 230 includes a patterned metal film deposited thereon, the metal film constituting working electrode 41, counter electrode 42, and detection electrode 43. Detection electrode 43 may not be provided. In addition to working electrode 41, counter electrode 42, and detection electrode 43, a Hct (hematocrit) electrode for measuring a hematocrit level can also be disposed to constitute a quadruple-electrode structure.

Specifically, a metal film as a conductive layer (not shown in the drawing) having an approximately uniform thickness is formed on the surface of sensor base 230. The respective electrodes may be formed on sensor base 230 by forming patterns by means of printing techniques using a conductive material. Alternatively, the electrode patterns may be formed by forming non-conductive tracks by laser ablation or the like of a conductive material (metal film) deposited on the surface of sensor base 230. For the material constituting the conductive layer, palladium, gold, platinum, carbon, and the like are preferable, with palladium being particularly preferable. For example, a conductive layer is formed by deposition of a film of palladium on the surface of sensor base 230 by sputtering, followed by formation of non-conductive tracks by laser ablation to form patterns of electrode. The width of the non-conductive track is preferably 0.01 mm to 0.5 mm, and more preferably 0.05 mm to 0.3 mm.

The thickness of the conductive layer formed on the surface of sensor base 230 can be changed according to the formation method and the constituent material thereof. For example, when the conductive layer is formed by sputtering, the thickness of the conductive layer is preferably 0.1 nm to 20 nm, and more preferably 1 nm to 10 nm. When the conductive layer is formed by printing techniques, the thickness of the conductive layer is preferably 0.1 µm to 50 µm, and more preferably 1 µm to 30 µm.

Sensor base 230 is formed of a material having an insulation property, e.g., resin such as polyethylene terephthalate, vinyl polymer, polyimide, polyester or styrenics; glass; or ceramics. The size of sensor base 230 is not limited to a specific numerical value. For example, the width of sensor base 230 is preferably 3 mm to 20 mm, and more preferably 5 mm to 10 mm. The length of sensor base 230 is preferably 20 mm to 40 mm. The thickness of sensor base 230 is preferably 0.1 mm to 1 mm. All of the width, length, and thickness of sensor base 230 are preferably within the above-described ranges.

Reagent 80 is disposed between sensor base 230 and spacer 220. Reagent 80 may be disposed so as to contact at least a portion of working electrode 41 and counter electrode 42. In addition reagent 80 may be disposed so as to also contact detection electrode 43. The composition of reagent 80 is appropriately selected according to the type of a substrate to be measured. Generally, a reagent includes an enzyme, a mediator and the like.

Slit 225 is formed in spacer 220. Slit 225 serves as a flow channel 240 for the injected biological sample. Flow channel 240 preferably communicates with, biological sample inlet 30. Flow channel 240 is preferably a capillary flow channel, and it is preferable that the liquid biological sample have capillary action. This allows the biological sample landed on biological sample inlet 30 to smoothly flow into flow channel 240 to reach reagent 80.

Air hole 215 is formed in cover 210, and communicates with the end of slit 225. Air hole 215 is preferably formed at a position away from biological sample inlet 30, i.e., inner part of flow channel 240 when viewed from biological sample inlet 30. When air hole 215 is provided in this way, it promotes a liquid biological sample to flow along the biological capillary flow channel. That is, air hole 215 plays a role of enhancing the capillary action (capillary phenomenon) so that the biological sample landed on biological sample inlet 30 smoothly flows into flow channel 240.

A liquid biological sample is injected through biological sample inlet 30, flows through flow channel 240 constituted by slit 225, and reaches reagent 80, where it dissolves reagent 80.

Thereafter, a potential difference is created between working electrode 41 and counter electrode 42 (i.e., voltage is applied between working electrode 41 and counter electrode 42), and a current flowing in the sample solution into which reagent 80 is dissolved is measured. Based on the measured value, the presence or concentration of a substrate (measurement target) contained in the biological sample are determined.

[Regarding Differentiation of Type of Biological Sample Measurement Sensor]

If it is possible to employ a plurality of types of biological sample measurement sensors in a single biological sample measurement device, it is more convenient for users. To achieve this, it is required for the biological sample measurement device to be able to differentiate numerous types of biological sample measurement sensors. The biological sample measurement device of the present invention is characterized by having a light-emitting element and a light-receiving element and differentiating numerous types of biological sample measurement sensors by using the light-emitting element and the light-receiving element.

Figure 15:
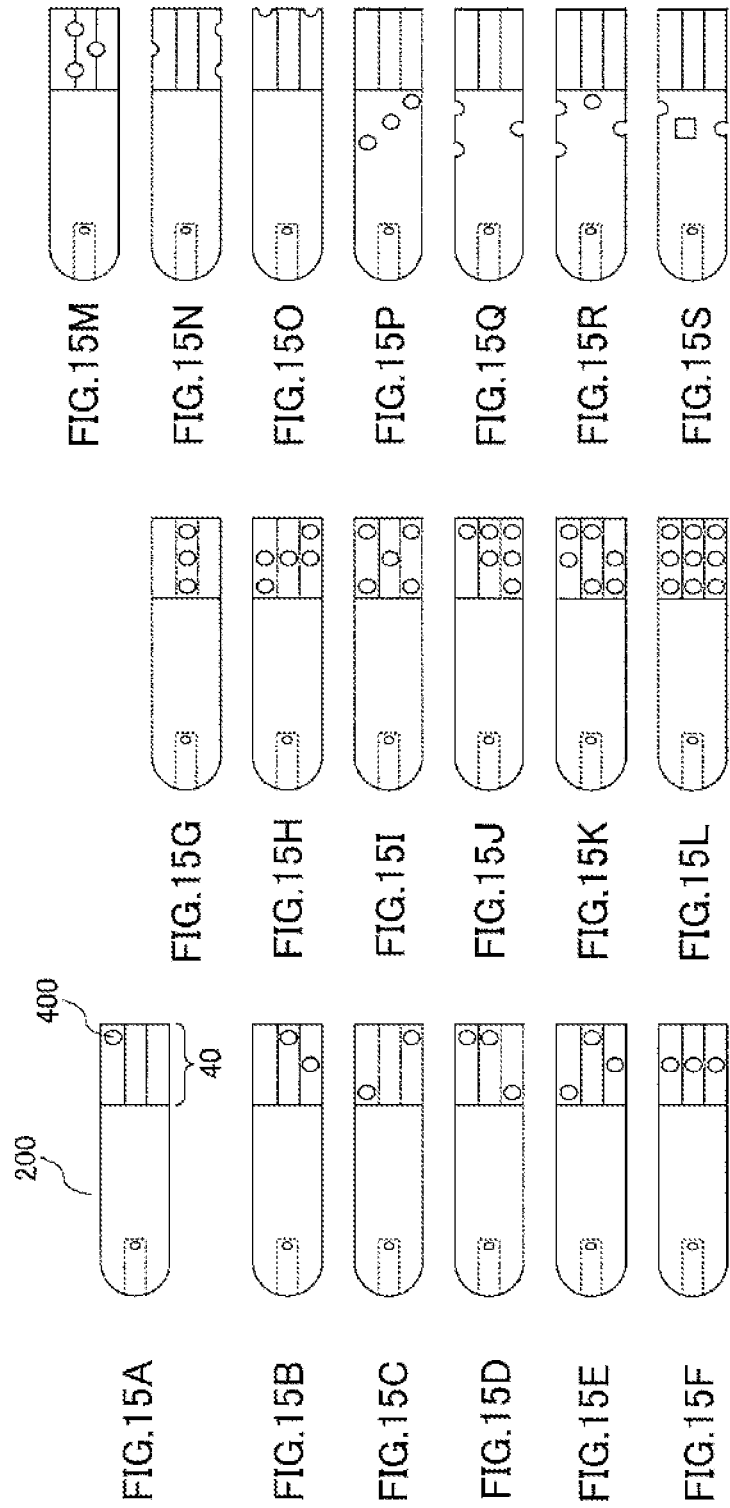
FIGS. 15A to 15S show biological sample measurement sensors having a light-transmissive section, which is to be attached to the biological sample measurement device of Embodiment 2.

The biological sample measurement sensor of the present invention preferably has a colored section (see FIG. 10 and Embodiment 1) or a light-transmissive section (see FIG. 15 and Embodiment 2). A biological sample measurement device having a color sensor can determine the type of a sensor having a colored section (see FIG. 7). A biological sample measurement device having a photodiode can determine the type of a biological sample measurement sensor having a light-transmissive section (see FIG. 12).

Figure 10A:
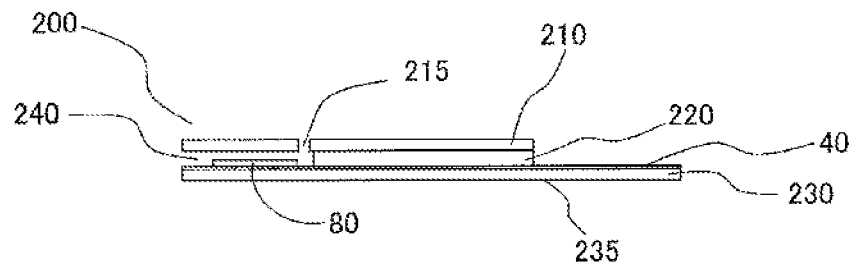
FIGS. 10A to 10C show biological sample measurement sensors having a colored section, which is to be attached to the biological sample measurement device of Embodiment 1.
Figure 10B:
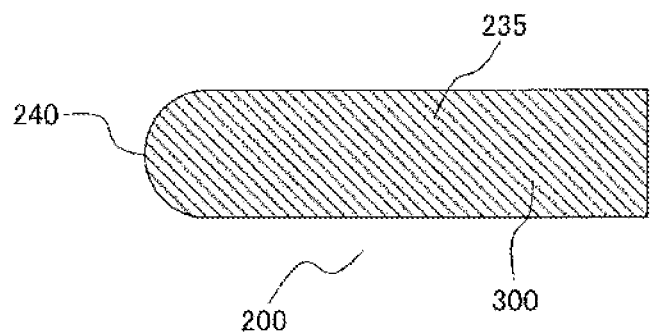
Figure 10C:
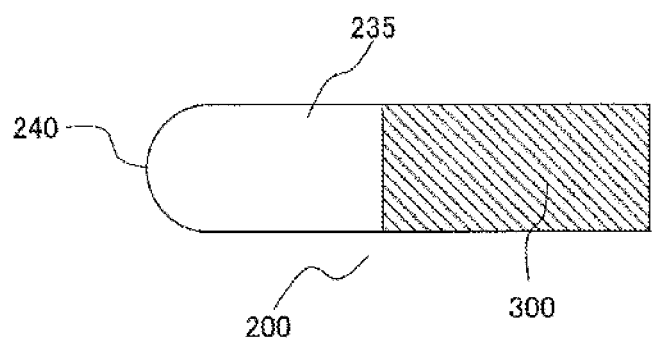

FIGS. 10A to 10C show examples of biological sample measurement sensor 200 having colored section 300. FIG. 10A is a cross-sectional view of biological sample measurement sensor 200 (see FIG. 4). Colored section 300 is preferably disposed on back surface 235 of sensor base 230. FIGS. 10B and 10C show back surface 235 of sensor base 230, specifically, the surface of sensor base 230 that is opposite to the surface where connection terminal section 40 is disposed.

As shown in FIG. 10B, colored section 300 may be disposed, on the entire surface of back surface 235 of sensor base 230; however, colored section 300 may be disposed in an area to be irradiated with light emitted from the light-emitting element of the biological sample measurement device. For example, as shown in FIG. 10C, colored section 300 may be disposed on the back surface of sensor base 230 in a region corresponding to connection terminal section 40 or a surrounding region thereof, when biological sample measurement sensor 200 is attached to sensor insertion port 7 of device main body 1 (see FIG. 7).

Specifically, colored section 300 may be inserted into device main body 1 with biological sample measurement sensor 200 being attached to sensor insertion port 7 shown in FIG. 7. For example, about ⅔ of the entire biological sample measurement sensor 200 inserted from sensor insertion port 7 is accommodated inside device main body 1. In this case, colored section 300 may cover, from the end of connection terminal section 40, about ⅔ of the entire hack surface 235 of biological sample measurement sensor 200. Needless to say, colored section 300 may cover smaller areas.

The biological sample measurement device of Embodiment 1 of the present invention has a light-emitting element and a light-receiving element. The light-emitting element applies light to the colored section, and the light-receiving element receives the light reflected from the colored section. By recognizing the color of the colored section, the light-receiving element can differentiate the type of a biological sample measurement sensor.

FIG. 15 shows an example of biological sample measurement sensor 200 having light-transmissive section 400. Light-transmissive section 400 may be a through hole formed in connection terminal section 40 of biological sample measurement sensor 200. FIG. 15 shows 19 types (15A to 15S) of arrangement patterns of light-transmissive section 400. In connection terminal section 40 of the sensor, a maximum of 9 through holes are formed (see 15L). As shown in 15N to 15S of FIG. 15, the through hole may be a notched semicircle or other shape.

In addition, 15P to 15S of FIG. 15 show examples in which light-transmissive section 400 is disposed at a position other than connection terminal section 40. When light-transmissive section 400 is disposed, at a position other than connection terminal section 40, the interference of connector terminal 17, flexure section 17a or the like that comes in contact with connection terminal section 40 is reduced, and therefore light-emitting element 12, light-receiving element 14, and the like may be more freely arranged. In addition, biological sample measurement sensors 200 shown in 15R and 15S of FIG. 15 include light-transmissive section 400 formed of notched semicircles, and light-transmissive section 400 formed of circular or tetragonal through holes.

Moreover, unlike other sensors, biological sample measurement sensor 200 shown in 15S of FIG. 15 has connection terminal section 40 having four electrodes (i.e., a working electrode, a counter electrode, a detection electrode, and a Hct electrode).

The number of light-transmissive section 400 (through hole) formed in biological sample measurement sensor 200 is not particularly limited, and is generally about 1 to 10. When the through hole is formed in connection terminal section 40 (cases shown in FIGS. 15A to 15L), the diameter of the through hole may be smaller than the width of the terminal section (conductive portion) corresponding to each electrode of connection terminal section 40. In addition, when the through hole is formed at a position other than the portion of connection terminal section 40 (cases shown in FIGS. 15M to 15S), the foregoing restriction is not imposed. Generally, the diameter of the through hole is about 0.05 mm to 5 mm, and preferably about 0.1 mm to 2 mm.

Light-transmissive section 400 disposed in the biological sample measurement sensor may be disposed at a position other than connection terminal section 40.

As described above, the shape of light-transmissive section 400 is not limited and can be circular, polygonal, semicircular, concave, wedged and/or the like. Moreover, light-transmissive section 400 is disposed in connection terminal section 40 and a surrounding region thereof; a central region of biological sample measurement sensor 200 other than connection terminal section 40 and a surrounding region thereof; lateral surface or end surfaces of biological sample measurement sensor 200; and so forth. The shape and arrangement of light-transmissive section 400 can be optionally selected and combined. In this way, the practicality of the biological sample measurement sensor of the present invention is enhanced.

The biological sample measurement device of Embodiment 2 of the present invention includes a light-emitting element and a light-receiving element. The light-emitting element applies light to the light-transmissive section formed of a through hole, and the light-receiving element receives the light passed through the light-transmissive section formed of a through hole. The light-receiving element recognizes the arrangement pattern of the through holes, whereby the type of biological sample measurement sensor can be differentiated.

As a method of detecting the pattern of light-transmissive section 400, an example of an optical detection method using light-emitting element 12 and light-receiving element 14 has been described above. However, the present invention is not limited to the optical detection method. For example, mechanical detection may be employed wherein a plurality of detection pins corresponding to respective holes of light-transmissive section 400 are provided. Alternatively, the presence of a semicircular and/or concave notch provided on the lateral surface/end surface of biological sample measurement sensor 200 can be mechanically detected, by means of detection pins from the lateral surface of the sensor.

In this manner, the biological sample measurement device of the present invention can differentiate the type of a biological sample measurement sensor by combining the light-emitting element with the light-receiving element; however, the biological sample measurement device can differentiate numerous types of biological sample measurement sensors by combining additional means with these elements. Examples of the additional include reading the pattern of the connection terminal section of the biological sample measurement sensor by using a connector terminal of the biological sample measurement device. This technique is disclosed in WO2003/076918.

As described above, biological sample measurement sensor 200 includes connection terminal section 40 (see FIG. 5). By changing the pattern of the connection terminal section 40 according to the type of biological sample measurement sensor 200, the biological sample measurement device can determine the type of biological sample measurement sensor 200.

FIG. 6 shows three examples of pattern (6A to 6C) of connection terminal section 40 of biological sample measurement sensor 200. The biological sample measurement device includes six connector terminals A to F which contact areas A to F, respectively.

Figure 6C:
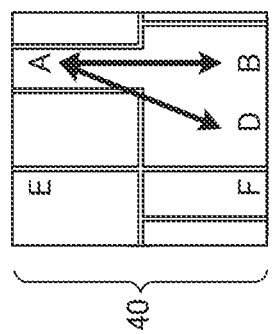
FIGS. 6A to 6C show examples of a pattern of a connection terminal section of the biological sample measurement sensor to be attached to the biological sample measurement device.
Figure 6B:
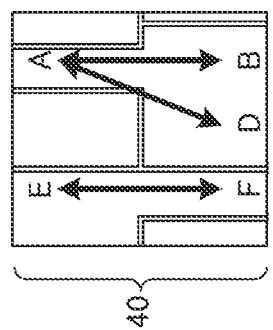
Figure 6A:
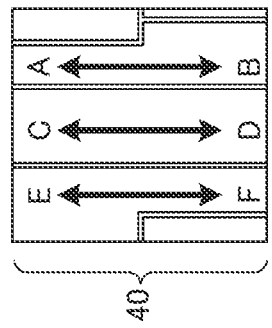

According to the pattern shown in FIG. 6A, among the six connector terminals A to F, A is conductive with B and D (indicated by "O" in the table). According to the pattern shown in FIG. 6B, among the six connection terminal sections A to F, A is conductive with B and D, and E is conductive with F. According to the pattern shown in FIG. 6C, among the six connector terminals A to F, A is conductive with B, C is conductive with D, and E is conductive with F. These results are summarized in the following table.

TABLE 1

| Type | Terminal-Terminal | | | |
| --- | --- | --- | --- | --- |
|  | A-B | A-D | C-D | E-F |
| a | O | O | X | X |
| b | O | O | X | O |
| c | O | X | O | O |

Accordingly, the biological sample measurement device having six connector terminals A to F can differentiate the patterning shown in FIGS. 6A to 6C. That is, when the value of electric resistance between, connector terminals of the biological sample measurement device is measured, three types of pattern can be differentiated.

In this manner, the patterns shown in FIGS. 6A to 6C can be differentiated based on whether or not connector terminals are conductive with each other. In addition, the connection terminal section of the biological sample measurement sensors may be patterned such that the value of electrical resistance varies among connector terminals. That is, when the value of electrical resistance is divided into three levels, it is possible to differentiate three different sensors by using two connector terminals. In this way, numerous types of sensors can be differentiated.

The number of connector terminals is not limited to 6. When the number of connector terminals is increased, it is possible to differentiate a larger number of sensor types.

As described above, in the biological sample measurement device of the present invention, a colored section (Embodiment 1) or a light-transmissive section (Embodiment 2) is disposed in the biological sample measurement sensor, whereby the type of the biological sample measurement sensor can be determined. Moreover, in the biological sample measurement device of the present invention, the connection terminal section of the biological sample measurement sensor is patterned, whereby the type of a larger number of biological sample measurement sensors can be determined. As a result, even when the type of sensors increases, the biological sample measurement device can differentiate each sensor from the other, and it is thus possible to perform appropriate measurement according to the type of sensor.

Hereinafter, embodiments of the present invention will be described in detail with reference to the accompanying drawings.

Embodiment 1

FIG. 7 shows the inside in the vicinity of connector 11 of biological sample measurement device 100 to which biological sample measurement sensor 200 has been attached (see FIG. 1). Liquid crystal display element 9 and the like are not illustrated in the drawing.

As described above, biological sample measurement sensor 200 is composed of cover 210, spacer 220, and plate-like sensor base 230 (see FIGS. 3 to 5). In addition, biological sample inlet 30 is disposed at one end (left side of FIG. 7) of sensor base 230, and connection terminal section 40 is disposed at the other end (right side of FIG. 7) of sensor base 230 (see FIG. 5). Connection terminal section 40 is attached to biological sample measurement device 100 so as to face flexure section 17a of connector terminal 17.

In addition, as shown in FIG. 10, colored section 300 is disposed on back surface 235 of sensor base 230 of biological sample measurement sensor 200. Colored section 300 may be colored with any color, e.g., white, blue or green. Colored section 300 may be disposed over the entire surface of back surface 235 or may be disposed only on a portion of back surface 235. For example, colored section 300 may be disposed only on a portion that comes in contact with transparent cover 16 (see FIG. 7).

Colored section 300 may also be disposed on a plurality of portions of back surface 235, with each colored section 300 having a different color. When a plurality of colored sections 300 is disposed, it is preferable to dispose a plurality of light-receiving elements 14 (color sensors) corresponding to the respective colored sections 300.

Different colors for colored section 300 can indicate different types of biological sample measurement sensor 200, the details of which will be described later. For example, a biological sample measurement sensor having white-colored section 300 can be a sensor for measuring a blood glucose level for 5 seconds; a biological sample measurement sensor having a blue-colored section 300 can be a sensor for measuring a blood glucose level for 7 seconds; and a biological sample measurement sensor having green-colored section 300 can be a sensor for measuring a lactic acid level.

Light-emitting element 12 is composed of, for example, an LED. The light to be emitted from light-emitting element 12 may be white light or colored light. Light-receiving element 14 is a color sensor. The color sensor may be able to detect three colors of RGB or detect a single color (any one of RGB). Light shielding plate 15 is disposed between light-emitting element 12 and light-receiving element 14. Light shielding plate 15 is, for example, a black non-reflective or low-reflective material. With light shielding plate 15, the light emitted from light-emitting element 12 is prevented from leaking toward light-receiving element 14. Therefore, the detection accuracy of light-receiving element 14 is improved, and as a result, the determination reliability of biological sample measurement sensor 200 is enhanced.

In addition, a transparent cover 16 that covers light-emitting element 12 and light-receiving element 14 is provided. The surface of transparent cover 16, which faces light-emitting element 12 and light-receiving element 14, contacts light shielding plate 15. By providing transparent cover 16, even if biological sample measurement sensor 200 is inserted into sensor insertion port 7 repeatedly, dust or the like is prevented from coming into contact with light-emitting element 12 and/or light-receiving element 14 (color sensor). Accordingly, the determination reliability of biological sample measurement sensor 200 is enhanced.

The surface of transparent cover 16 that faces away light-emitting element 12 and light-receiving element 14 is a contact surface that comes in contact with biological sample measurement sensor 200. Moreover, there are provided connector terminals 17 on the side of transparent cover 16 that faces away light-emitting element 12 and light-receiving element 14. Specifically, a plurality of connector terminals 17 is disposed at a predetermined interval.

Biological sample measurement sensor 200 is inserted into the measurement device through sensor insertion port 7 disposed in main body case 1, and disposed in the gap formed between the contact surface of transparent cover 16 and connector terminal 17.

Connector terminal 17 is disposed in connector 11. Flexure section 17a as a portion of connector terminal 17 can be connected, to connection terminal section 40 (see FIG. 10) of the attached biological sample measurement sensor 200. Flexure section 17a of connector terminal 17 can press colored section 300 of biological sample measurement sensor 200 against the contact surface of transparent cover 16. Consequently, light emitted from light-emitting element 12 can appropriately reach the colored section. Therefore, the determination reliability of biological sample measurement sensor 200 is enhanced.

Flexure section 17a is preferably disposed closer to sensor insertion port 7 than is light shielding plate 15. In order to prevent biological sample measurement sensor 200 from being distorted near sensor insertion port 7 by receiving stress from flexure section 17a, it is preferable to provide flexure section 17a of connector terminal 17 closer to sensor insertion port 7 than is light shielding plate 15. If biological sample measurement sensor 200 is distorted near sensor insertion port 7, external light enters through sensor insertion port 7. In this way, by the position for disposing flexure section 17a, the determination reliability of biological sample measurement sensor 200 can be heightened.

As shown in FIG. 7, connector 11 includes light-emitting element 12 and light-receiving element 14 which are disposed in the lower portion inside main body case 1. Light-emitting element 12 emits light toward colored section 300 (see FIG. 10) of biological sample measurement sensor 200 attached to connector 11. The light passes through transparent cover 16 and is emitted to colored section 300 of biological sample measurement sensor 200. The light applied to biological sample measurement sensor 200 is reflected, and the reflected light is received by light-receiving element 14 (color sensor). The color of the reflected light is affected by colored section 300 of biological sample measurement sensor 200.

Figure 8:
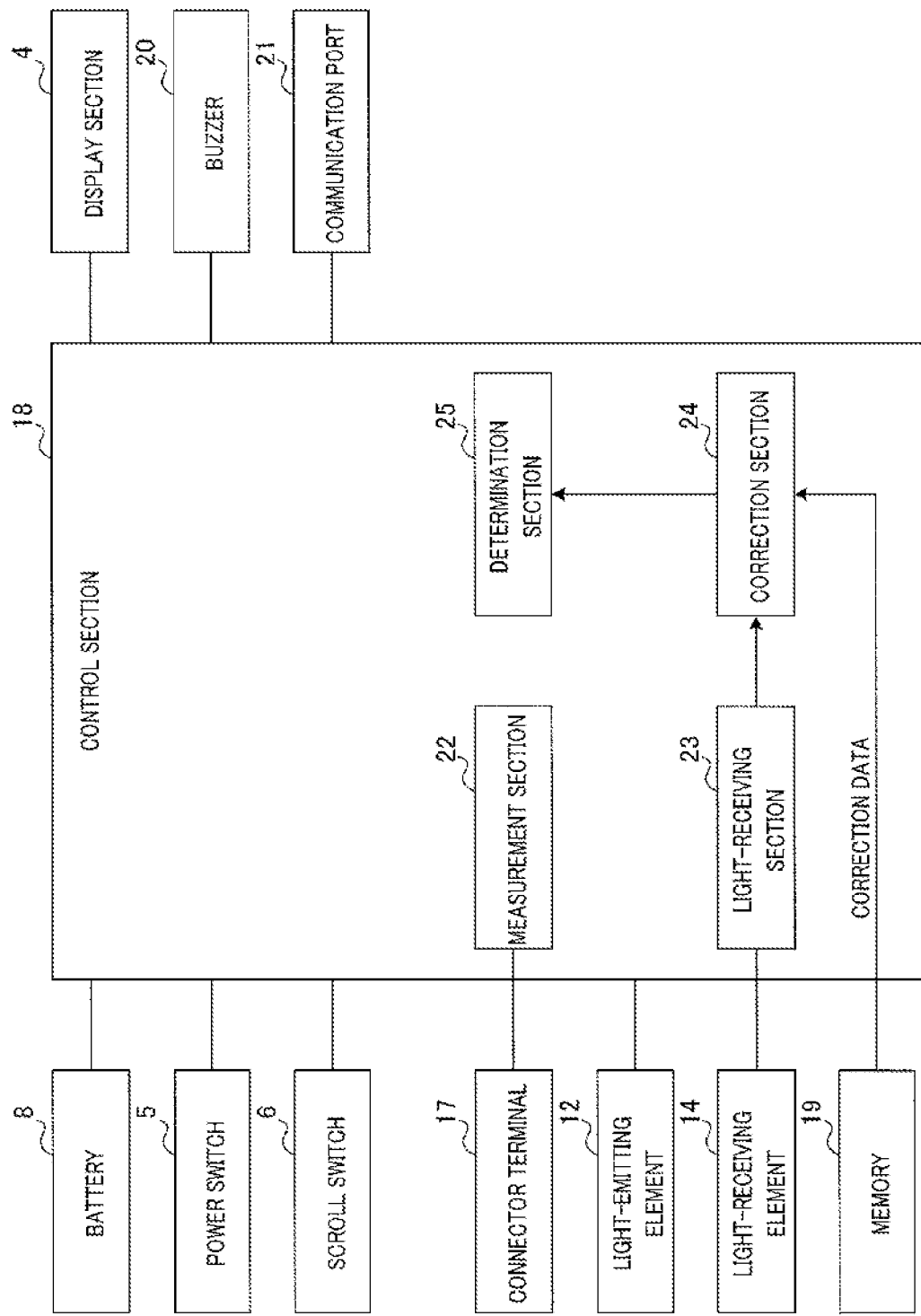
FIG. 8 is an electrical block diagram of the biological sample measurement device of Embodiment 1.

FIG. 8 is an electrical control block diagram of the biological sample measurement device shown in FIG. 7. Control section 18 composed of a microprocessor attached to control board 10 is connected to display section 4, power switch 5, scroll switch 6, battery 8, light-emitting element 12, light-receiving element 14, and connector terminal 17. Control section 18 is also connected to memory 19, buzzer 20, and communication port 21.

Connector terminal 17 is connected to measurement section 22, and light-receiving element 14 is connected to light-receiving section 23. Light-receiving section 23 and memory 19 are connected to correction section 24, and correction section 24 is connected to determination section 25.

Figure 9:
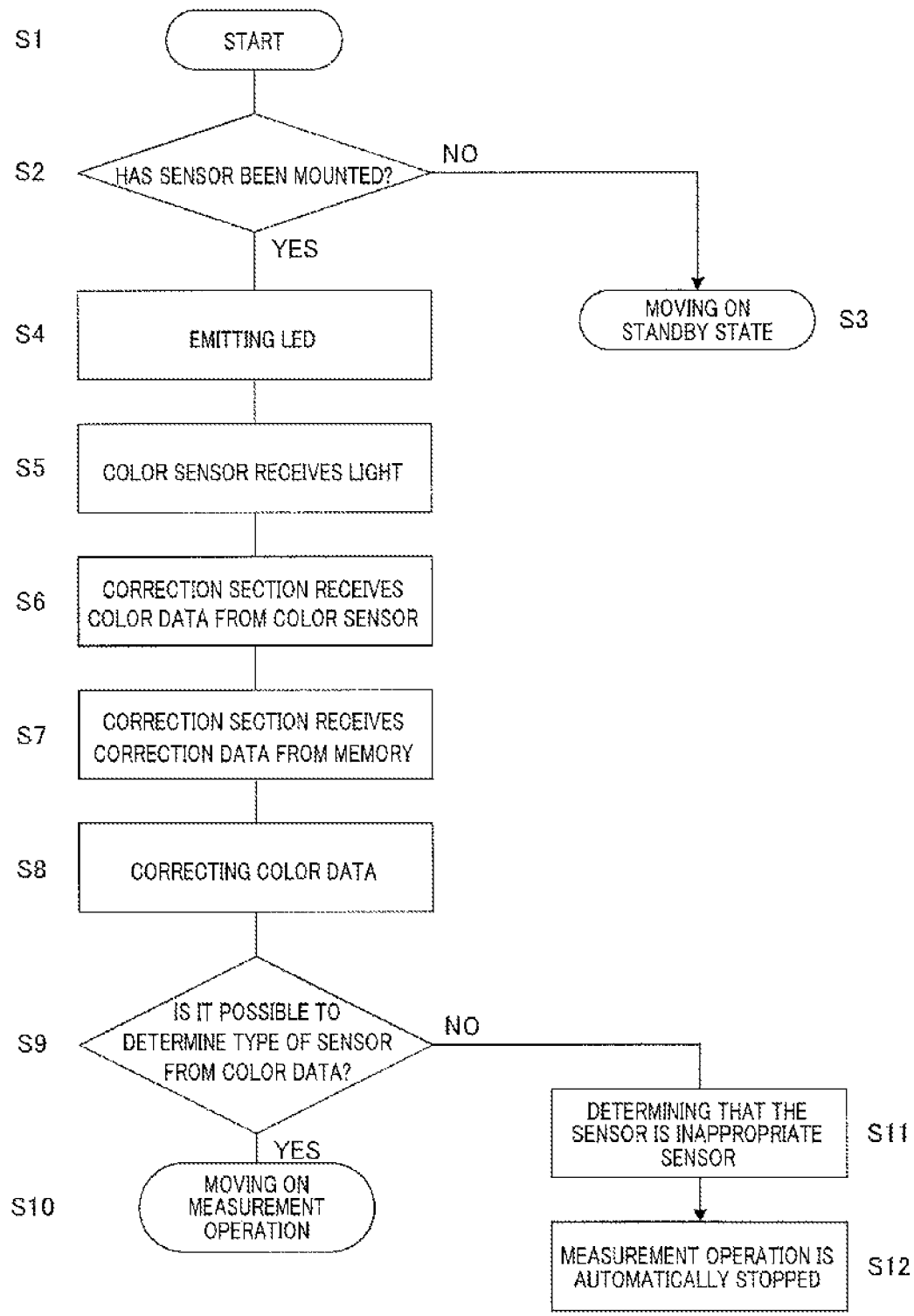
FIG. 9 is a flowchart of a measurement performed by the biological sample measurement device of Embodiment 1.

FIG. 9 shows the flow of an operation for determining the color of biological sample measurement sensor 200 that is performed by the biological sample measurement device shown in FIG. 7. When power switch 5 (sec FIG. 1) is turned on, the color determination operation is started (S1). When the color determination operation is started, it is determined whether or not biological sample measurement sensor 200 has been inserted into sensor insertion port 7 and attached to connector 11 (S2).

Specifically, attachment of biological sample measurement sensor 200 is determined by whether or not flexure section 17a of connector terminal 17 has been connected to connection terminal section 40 of biological sample measurement sensor 200. When it is determined that the sensor has not been attached, the device is placed in a standby state (S3).

When it is determined that the sensor has been attached, light-emitting element 12 (LED) emits light (S4). Then the light (e.g., white light) emitted from light-emitting element 12 passes through transparent cover 16 and is obliquely applied to back surface 235 of sensor base 230 of biological sample measurement sensor 200 (see FIG. 7). The emitted light is reflected from back surface 235 of sensor base 230. Light-receiving element 14 receives the reflected light that passed through transparent cover 16 (S5). Light-receiving element 14 as a color sensor transmits the color data of the light received via light-receiving section 23 to correction section 24 (S6).

Meanwhile, correction section 24 reads correction data stored in memory 19 (S7). Thereafter, based on the correction data thus read, correction section 24 corrects the color data received from light-emitting element 14 (color sensor) (S8). The color sensor has a sensitivity spectrum (a certain range of sensitivity). Therefore, it is preferable to correct the color data to convert the data into preset standard color data. In this manner, the determination (described later) performed in S9 has more accuracy.

The corrected color data is transmitted to determination section 25, and determination section 25 determines the type of biological sample measurement sensor 200 (S9). Specifically, the color of colored section 300 on back surface 235 of sensor base 230 of biological sample measurement sensor 200 is determined.

When the determination section fails to determine the color of colored section 300 in S9, the biological sample measurement sensor attached is determined to be an inappropriate sensor (S11), and the measurement operation is automatically stopped (S12).

As a result of the determination in S9, when the type of biological sample measurement sensor 200 can be determined, the process moves on an operation for measuring the biological sample (S10), and measurement section 22 measures the substrate in the biological sample. For example, when the color is determined to be white in S9, a blood glucose level is measured in measurement section 22 for 5 seconds; when the color is determined to be blue, a blood glucose level is measured in measurement section 22 for 7 seconds; and when the color is determined to be green, a lactic acid level is measured in measurement section 22.

As described above, Embodiment 1 enables to determine the type of biological sample measurement sensor 200 by the color of the sensor by means of light-emitting element 12 and light-receiving element 14 (color sensor). In addition, since users can easily recognize the color of colored section 300 of biological sample measurement sensor 200, the user can also easily differentiate the type of biological sample measurement sensor 200 by him/herself.

Biological sample measurement sensor 200 used in Embodiment 1 can be obtained by simply providing a colored section to a biological sample measurement sensor in the related art. Consequently, the sensor can be easily produced at a low cost.

The type of biological sample measurement sensor 200 may be differentiated not only by using the colored section as in Embodiment 1, but also by reading the pattern such as that shown in FIG. 6 of connection terminal section 40 of biological sample measurement sensor 200 by using connector terminal 17 of biological sample measurement device 100. That is, when recognition of color of biological sample measurement sensor 200 described above is combined with the pattern of connection terminal section 40, it is possible to differentiate more various types of biological sample measurement sensors.

Modified Example of Embodiment 1

In Embodiment 1, as shown in FIG. 7, colored section 300 is disposed on the back surface of biological sample measurement sensor 200 in a region corresponding to connection terminal section 40 (i.e., a surface that is opposite to the surface to which connector terminal 17 contacts) (see FIG. 10), and when biological sample measurement sensor 200 is attached, colored section 300 is positioned inside connector 11. Accordingly, light-emitting element 12 and light-receiving element 14 (color sensor) are disposed inside connector 11.

Figure 11:
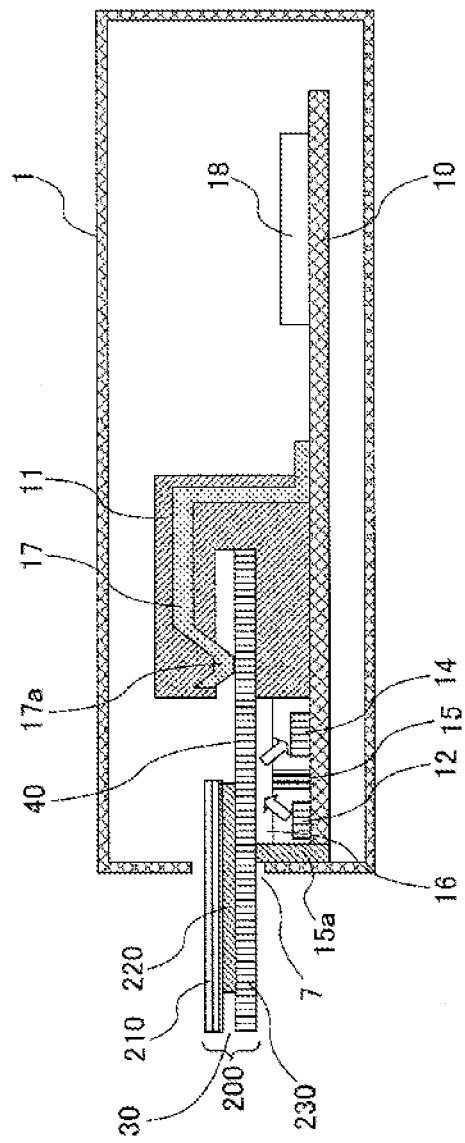
FIG. 11 is a main part cross-sectional view of the vicinity of a connector of a biological sample measurement device of a modified example of Embodiment 1.

In contrast, in this modified example, light-emitting element 12 and light-receiving element 14 (color sensor) are disposed outside connector 11, as shown in FIG. 11. In this case, when biological sample measurement sensor 200 is attached, colored section 300 of biological sample measurement sensor 200 is positioned outside connector 11. Except this point, this example is the same as the above example, and the same sections are marked with the same reference signs to skip the description thereof.

As shown in FIG. 11, light-emitting element 12 and light-receiving element 14 (color sensor) are disposed outside connector 11. Accordingly, light-emitting element 12 and light-receiving element 14 less interfere with connector 11, connector terminal 17, flexure section 17a, and the like. Therefore, the degree of freedom in arranging light-emitting element 12, light-receiving element 14 and the like is more improved, compared to Embodiment 1.

As shown in 11, when light-emitting element 12 and light-receiving element 14 (color sensor) are disposed outside connector 11, a second light shielding plate 15a is further disposed at sensor insertion port 7 side, whereby external light through sensor insertion port 7 of device main body 1 can be blocked. By blocking the external light, the detection accuracy of light-receiving element 14 is improved, and the reliability in color determination is improved.

In addition, light-emitting element 12, light-receiving element 14, or the like may be disposed on sensor insertion port 7 side (see FIG. 11) of connector 11 or besides connector 11 (inside of the paper in FIG. 11).

Also in the modified example of Embodiment 1, as shown in FIG. 6, the pattern of connection terminal section 40 of biological, sample measurement sensor 200 is read by the connector terminal of the biological sample measurement device, whereby the type of the biological sample measurement sensor 200 can be differentiated. That is, by combining the recognition of the color of biological sample measurement sensor 200 in the modified example of the above Embodiment 1 with the pattern of the connection terminal section, it is possible to differentiate more various types of biological sample measurement sensors.

Embodiment 2

As with FIG. 7, FIG. 12 shows the inside in the vicinity of connector 11 of the biological sample measurement device to which biological sample measurement sensor 200 has been attached. The same members as shown in FIG. 7 are marked with the same reference signs to omit the description thereof in some cases.

Biological sample measurement sensor 200 in Embodiment 2 is the same as biological sample measurement sensor 200 in Embodiment 1, except that the biological sample measurement sensor 200 of Embodiment 2 has light-transmissive section 400 (see FIG. 15). As shown in FIG. 15, biological sample measurement sensor 200 has light-transmissive section 400 including a through hole formed in connection terminal section 40.

Biological sample measurement sensor 200 is attached to the biological sample measurement device such that connection terminal, section 40 (see FIG. 15) faces flexure section 17a of connector terminal 17. Biological sample measurement sensor 200 is inserted into the measurement device through insertion port 7 disposed in main body case 1.

As shown in FIG. 12, connector 11 includes light-emitting element 12 facing one surface of biological sample measurement sensor 200 attached, and light-receiving element 14 facing other surface of biological sample measurement sensor 200 attached. In addition, light-emitting element 12 and light-receiving element 14 are covered with light shielding section 33. Particularly, it is preferable that light shielding section 33 be disposed such that light through insertion port 7 is blocked. Light shielding section 33 uses, for example, a non-reflective or low-reflective material of black color.

Connector 11 includes connector terminals 17. Specifically, a plurality of connector terminals 17 is disposed at a predetermined interval. Flexure section 17a, a portion, of connector terminal 17, can be connected to connection terminal section 40 of biological sample measurement sensor 200 attached.

Light-emitting element 12 emits light toward the through hole as light-transmissive section 400 of biological sample measurement sensor 200 attached to connector 11. The light passes through the through hole of biological, sample measurement sensor 200, and the transmitted light is received by light-receiving element 14 (photodiode). Light-receiving element 14 is a photodiode which is attached to circuit board 10 and electrically connected to control section 18.

It is preferable that one or more light-receiving elements 14 are disposed. The number of light-receiving elements 14 disposed is preferably the same as the maximum number of light-transmissive sections 400 that can be formed in biological sample measurement sensor 200. For example, in order to differentiate all biological sample measurement sensors having the patterns 15A to 15L of FIG. 15, it is preferable that nine light-receiving elements 14 (photodiode) be formed in the biological sample measurement device.

Light-receiving element 14 recognizes the arrangement pattern of the through holes that serve as light-transmissive section 400, whereby the type of biological sample measurement sensor 200 attached can be determined.

In addition, biological sample measurement sensor 200 of 15P to 15S of FIG. 15 includes light-transmitting section 400 not in connection terminal section 40, but in a region other than connection terminal section 40. Accordingly, the light-receiving elements (photodiode) are disposed not in the vicinity of connection terminal section 40 of biological sample measurement sensor 200 attached, but at positions away from the connection terminal section 40. Consequently, a problem hard to arise that the light to be received by the light-receiving element (photodiode) is interfered with by connector terminal 17 or flexure section 17a.

Biological sample measurement sensor 200 of 15N, 15O, and 15Q to 15S of FIG. 15 does not include light-transmissive section 400 formed of a through hole, but includes light-transmissive section 400 formed of a notch having a semicircular, concave, wedged or other shape disposed in the side surface or end surface of biological sample measurement sensor 200.

When the pattern of light-transmissive section 400 of biological sample measurement sensor 200 has such a notch shape as described above, the pattern may be optically detected using light-emitting element 12 and light-receiving element 14. In addition, the pattern can be mechanically detected using a method of recognizing the pattern of light-transmissive section 400 by bringing detection pins into contact with the biological sample measurement sensor 200 from the lateral surface, a method of using a micro switch, and the like.

Figure 13:
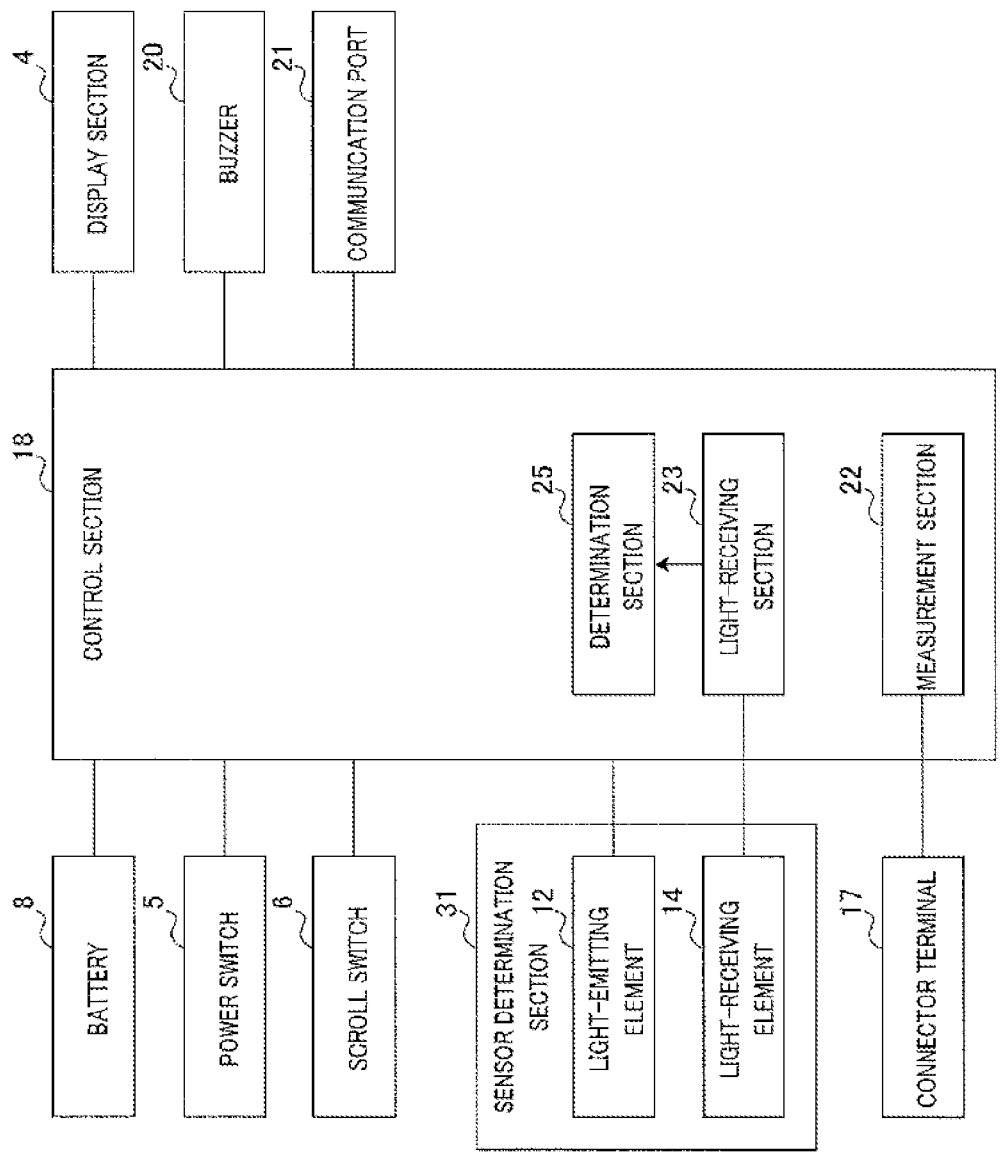
FIG. 13 is an electrical block diagram of the biological sample measurement device of Embodiment 2.

FIG. 13 is an electrical control block diagram of the biological sample measurement device shown in FIG. 12. Control section 18 formed of a micro processor attached to control board 10 is connected to display section 4, power switch 5, scroll switch 6, battery 8, light-emitting element 12, light-receiving element 14 (photodiode), and connector terminal 17. Control section 18 is also connected to buzzer 20 and communication port 21.

Connector terminal 17 is connected to measurement section 22, and light-receiving element 14 is connected to light-receiving section 23. Light-receiving section 23 is connected to determination section 25.

Figure 14:
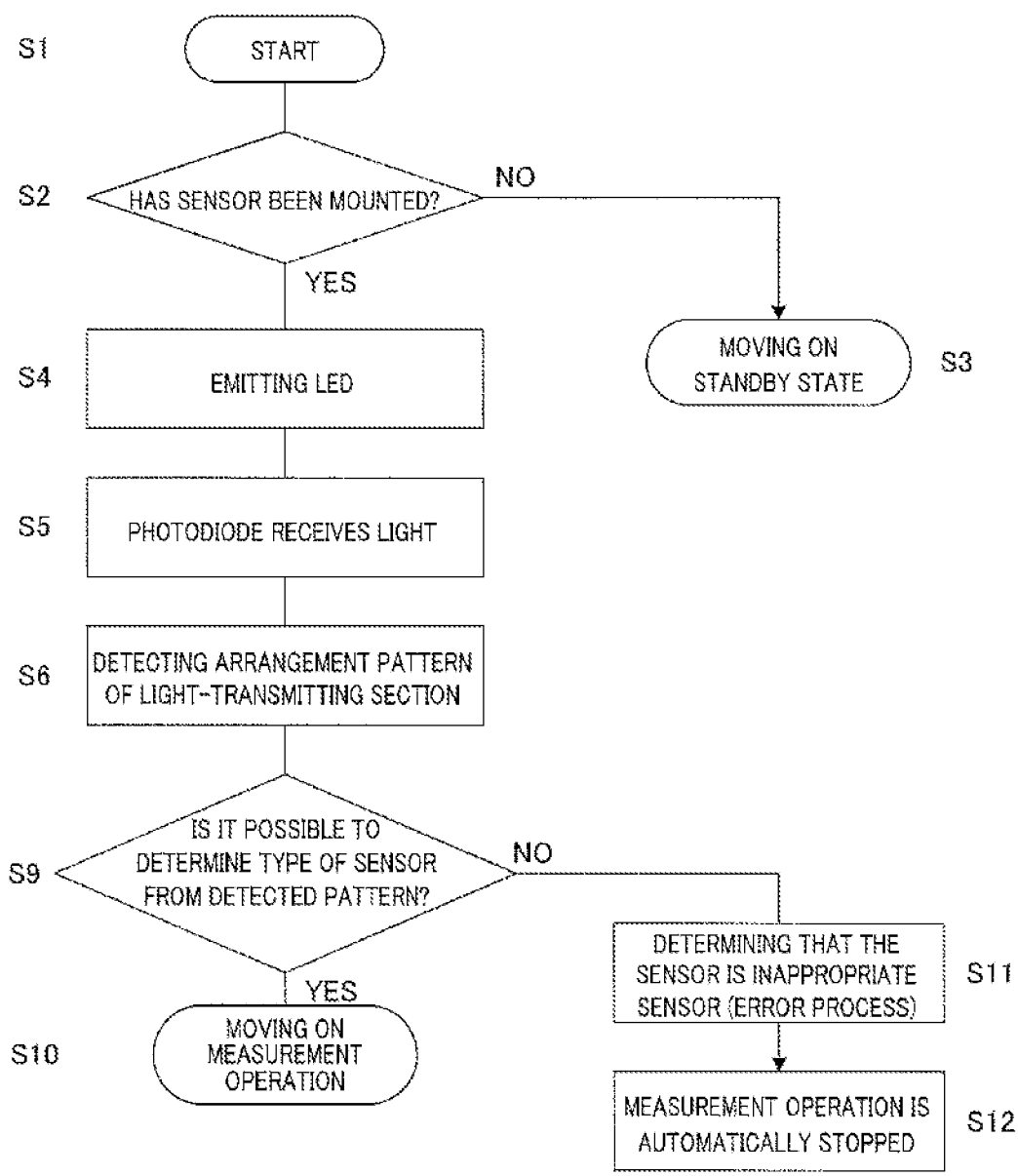
FIG. 14 is a flowchart of measurement performed by the biological sample measurement device of Embodiment 2.

FIG. 14 shows the flow of a determination operation for recognizing biological sample measurement sensor 200 by biological sample measurement device 100 (see FIG. 1) shown in FIG. 12. When power switch 5 (see FIG. 1) is turned on, the determination operation is started (S1). When the determination operation is started, it is determined whether or not biological sample measurement sensor 200 has been inserted into sensor insertion port 7 and attached to the biological sample measurement device (S2).

Specifically, attachment of biological sample measurement sensor 200 is determined by whether or not flexure section 17a of connector terminal 17 has been connected to the connection terminal section of biological sample measurement sensor 200. When no connection is detected, the device is placed in a standby state (S3).

When it is determined that biological sample measurement sensor 200 has been attached, light-emitting element 12 emits light (LED) (S4). Light (e.g., white light) emitted from light-emitting element 12 passes through light-transmissive section 400 of biological sample measurement sensor 200 (see FIG. 12). Light-receiving element 14 (photodiode) receives the transmitted light (S5). When a plurality of light-receiving elements 14 is provided, not all light-receiving elements 14 necessarily receive the transmitted light. Depending on the arrangement of light-transmissive sections 400, some of light-receiving elements 14 receive the transmitted light and some do not receive the transmitted light.

A signal from light-receiving element 14 that received light is input in light-receiving section 23 and transmitted to determination section 25 (see FIG. 13). Determination section 25 detects the arrangement pattern (the number and arrangement of the light-transmissive sections) of the light-transmissive section (S6). From the arrangement pattern detected, determination section 25 determines the type of biological sample measurement sensor 200 (S9).

When determination section 25 fails to determine the type of biological sample measurement sensor 200 in S9, it is determined that the attached sensor is an inappropriate sensor. Accordingly, an error process is performed (S11), and the measurement operation is automatically stopped (S12). At this time, an error code or error message may be displayed on display section 4, or warning sound may be played by buzzer 20.

When the type of biological sample measurement sensor 200 can be determined as a result of the determination in S9, the process moves on the measurement operation of a biological sample (S10), and measurement section 22 measures the substrate in the biological sample.

The accuracy in detecting the presence or absence of the transmitted light by a photodiode as in Embodiment 2 tends to be higher than the accuracy in detecting color information by the color sensor as in Embodiment 1. Accordingly, according to Embodiment 2, the type of a biological sample measurement sensor can be more accurately determined in some cases.

In addition, the type of biological sample measurement sensor 200 may be differentiated by the light-transmissive section of Embodiment 2. and at the same time by reading the pattern of connection terminal section 40 of biological sample measurement sensor 200 by means of the connector terminal of the biological sample measurement device as shown in FIG. 6. That is, by combining the recognition of biological sample measurement sensor 200 by using the above light-transmissive section with the pattern of the connection terminal section, it is possible to differentiate more various types of biological sample measurement sensors.

Modified Example of Embodiment 2

In Embodiment 2, light-transmissive section 400 is provided in biological sample measurement sensor 200 at the position of connection terminal section 40, and light-transmissive section 400 is positioned inside connector 11 when biological sample measurement sensor 200 is attached, as shown in FIG. 12. Accordingly, light-emitting element 12 and light-receiving element 14 (photodiode) are disposed inside connector 11.

Figure 16:
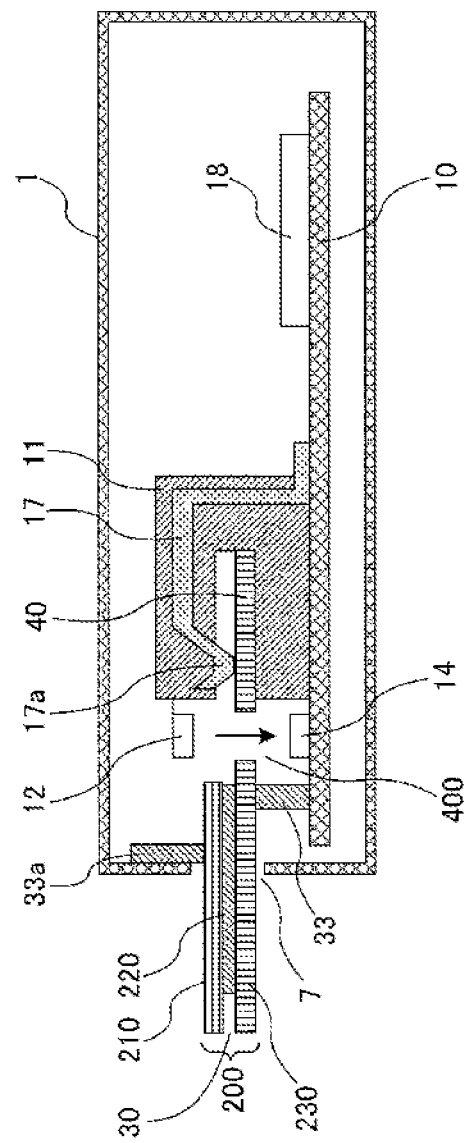
FIG. 16 is a main part cross-sectional view of the vicinity of a connector of a biological sample measurement device of a modified example of Embodiment 2.

In contrast, in the present embodiment, light-emitting element 12 and light-receiving element 14 (photodiode) are disposed outside connector 11, as shown in FIG. 16. In this case, light-transmissive section 400 of biological sample measurement sensor 200 is positioned outside connector 11, when biological sample measurement sensor 200 is attached. The present example is the same as the above example except for this point, and the same sections are marked with the same reference signs to skip the description thereof.

As shown in FIG. 16, since light-emitting element 12 and light-receiving element 14 (photodiode) are disposed outside connector 11, light-emitting element 12 and light-receiving element 14 less interfere with connector 11, connector terminal 17, flexure section 17a and the like. Consequently, the degree of freedom in arranging light-emitting element 12, light-receiving element 14, and the like is more improved, compared to Embodiment 1.

Examples of the pattern of light-transmissive section 400 of biological sample measurement sensor 200 used in the present modified example are shown in 15P to 15S of FIG. 15. In biological sample measurement sensor 200 of FIG. 15P, light-transmissive section 400 formed of a plurality of circular through holes is disposed in a region other than connection terminal section 40. In this case, it is advantageous to provide a plurality of light-receiving elements 14. In biological sample measurement sensor 200 of 15Q of FIG. 15, light-transmissive section 400 formed of notches is provided in the lateral, surface of biological sample measurement sensor 200 in a region other than connection terminal section 40.

Biological sample measurement sensor 200 of 15R shown in FIG. 15 shows an example in which light-transmissive section 400 formed of a through hole shown in 15P shown FIG. 15 is combined with light-transmissive section 400 formed of notches shown in 15Q shown in FIG. 15. Similarly to the biological sample measurement sensor of 15R shown in FIG. 15, the biological sample measurement sensor of 15S shown in FIG. 15 includes light-transmissive section 400 formed of a through hole and light-transmissive section 400 formed of notches. This sensor shows a case where the shape of the hole of light-transmissive section 400 formed of a through hole is a polygon such as tetragon, and connection terminal section 40 has four electrodes. The four electrodes include a working electrode, a counter electrode, a detection electrode, and a Hct electrode.

In addition, as shown in FIG. 16, a second light shielding section 33a for blocking external light may be disposed at sensor insertion port 7 side of device main body 1. When the external light is blocked, the accuracy in detecting the pattern of light-transmissive section 400 by means of light-receiving element 14 is improved, and determination reliability is improved.

Also in the modified example of Embodiment 2, the pattern of connection terminal section 40 of biological sample measurement sensor 200 is read by the connector terminal of the biological sample measurement device as shown in FIG. 6, whereby the type of biological sample measurement sensor 200 can be differentiated. That is, by combining the recognition of biological sample measurement sensor 200 by means of light-transmissive section 400 in the above modified example of Embodiment 2 with the pattern of the connection terminal section, it is possible to differentiate more various types of biological sample measurement sensors.

The color-based sensor recognition system described in Embodiment 1 and the sensor recognition system using light-transmissive section 400 demonstrated in Embodiment 2 have been described above. The systems may be used independently or in combination. Moreover, in addition to the combination, when the pattern of connection terminal section 40 is read by connector terminal 17 of biological sample measurement device 100, it is also possible to differentiate the type of biological sample measurement sensor 200.

INDUSTRIAL APPLICABILITY

Unlike the conventional measurement devices that use a barcode reader, the biological, sample measurement device of the present invention can determine the type of a large number of biological sample measurement sensors, without requiring means for scanning light or means for reading the scanned light. Therefore, the device of the present invention can relatively, easily, and sufficiently respond to the increase in the type of biological sample measurement sensors that will be caused by the increase in the application or the type of devices that may be required in the future. Accordingly, it is possible to reduce the cost of the biological sample measuring device. Consequently, for example, utilization of the biological sample measurement device is expected.

REFERENCE SIGNS LIST

1 Main body case
2 Top cover
3 Bottom cover
4 Display section
5 Power switch
6 Scroll switch.
7 Sensor insertion port
8 Battery
9 Liquid crystal display element
10 Control board
11 Connector
12 Light-emitting element
14 Light-receiving element
15 Light shielding plate
16 Transparent cover 17 Connector terminal
17a Flexure section
18 Control section
19 Memory
20 Buzzer
21 Communication port
22 Measurement section
23 Light-receiving section
24 Correction section
25 Determination section
30 Biological sample inlet
31 Sensor determination section
33 Light shielding section
40 Connection terminal section
80 Reagent
100 Biological sample measurement device
200 Biological sample measurement sensor
210 Cover
215 Air hole
220 Spacer
225 Slit
230 Sensor base
235 Back surface of sensor base
240 Flow channel
300 Colored section
400 Light-transmissive section

The invention claimed is:

1. A biological sample measurement device comprising:
a main body case having a sensor insertion port which is for inserting a biological sample measurement sensor having a colored section;
a connector which is disposed in the main body case and which is configured to attach the biological sample measurement sensor;
a light-emitting element which is disposed in the main body case and which is configured to apply light to the colored section of the biological sample measurement sensor attached to the connector;
a light-receiving element which is disposed in the main body case and which is configured to receive the light reflected from the colored section of the biological sample measurement sensor attached to the connector, and output a color data of the received light;
a connector terminal which is disposed in the main body case and can be connected to a connection terminal section of the biological sample measurement sensor attached to the connector;
a determination section which is configured to determine a type of the biological sample measurement sensor attached to the connector based on the color data; and
a measurement section which is configured to measure a substrate in the biological sample in the biological sample measurement sensor attached to the connector based on the determination result of the determination section.

2. The biological sample measurement device according to claim 1,
wherein the light-receiving element is a color sensor.

3. The biological sample measurement device according to claim 2, further comprising:
a light shielding plate disposed between the light-emitting element and the light-receiving element.

4. The biological sample measurement device according to claim 3,
wherein a position where the connector terminal is connected to the connection terminal section of the biological sample measurement sensor is closer to the sensor insertion port than is the light shielding plate.

5. The biological sample measurement device according to claim 1, further comprising:
a transparent cover that covers the light-emitting element and the light-receiving element,
wherein a surface of the transparent cover that faces away the light-emitting element and the light-receiving element is a contact surface that comes in contact with the biological sample measurement sensor to be attached to the connector.

6. The biological sample measurement device according to claim 5,
wherein the connector terminal is disposed on a side of the transparent cover, the side facing away the light-emitting element and the light-receiving element.

7. The biological sample measurement device according to claim 5,
wherein the biological sample measurement sensor to be inserted through the sensor insertion port is to be inserted between the contact surface of the transparent cover and the connector terminal.

8. The biological sample measurement device according to claim 1, further comprising:
a correction section which is configured to correct the color data outputted from the light-receiving element to a preset standard color data,
wherein the determination section determines the type of the biological sample measurement sensor attached to the connector based on the color data corrected in the correction section.

9. The biological sample measurement device according to claim 1,
wherein the measurement section stops the measurement operation when the determination section fail to determine the color of the color section.

10. The biological sample measurement device according to claim 1,
wherein the color section is disposed on a part or whole surface opposite to an arrangement surface of the connection terminal section of the biological sample measurement sensor; and
the light-emitting element and the light-receiving element are arranged on the opposite surface arranged the connector terminal.

11. The biological sample measurement device according to claim 1,
wherein a plurality of the light-receiving element are disposed.

* * * * *